(12) United States Patent
Du et al.

(10) Patent No.: US 8,635,258 B2
(45) Date of Patent: Jan. 21, 2014

(54) ALIGNMENT OF MULTIPLE LIQUID CHROMATOGRAPHY-MASS SPECTROMETRY RUNS

(75) Inventors: Peicheng Du, Yorktown Heights, NY (US); Frank Suits, Garrison, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/598,959

(22) Filed: Aug. 30, 2012

(65) Prior Publication Data
US 2012/0323985 A1    Dec. 20, 2012

Related U.S. Application Data

(63) Continuation of application No. 12/546,966, filed on Aug. 25, 2009.

(51) Int. Cl.
G06F 7/00    (2006.01)
G06F 15/00    (2006.01)

(52) U.S. Cl.
USPC .......................................... 708/207

(58) Field of Classification Search
None
See application file for complete search history.

(56) References Cited

U.S. PATENT DOCUMENTS

| | | | |
|---|---|---|---|
| 6,694,343 B2 | 2/2004 | Forrest et al. | |
| 6,936,814 B2* | 8/2005 | Hastings | 250/282 |
| 6,957,473 B2* | 10/2005 | Nishikori et al. | 15/359 |
| 6,989,100 B2 | 1/2006 | Norton | |
| 7,089,275 B2 | 8/2006 | Garg | |
| 7,158,903 B2 | 1/2007 | Kushnir et al. | |
| 2002/0077789 A1 | 6/2002 | Mitsunaga et al. | |
| 2004/0113062 A1* | 6/2004 | Norton | 250/282 |
| 2004/0253147 A1* | 12/2004 | Golushko | 422/71 |
| 2005/0109928 A1* | 5/2005 | Hastings | 250/281 |
| 2006/0287834 A1* | 12/2006 | Kearney et al. | 702/27 |
| 2007/0038386 A1* | 2/2007 | Schadt et al. | 702/20 |
| 2007/0239642 A1 | 10/2007 | Sindhwani et al. | |
| 2007/0255779 A1 | 11/2007 | Watts | |
| 2008/0052337 A1 | 2/2008 | Adams | |

FOREIGN PATENT DOCUMENTS

WO    WO2006125864 A1    11/2006

OTHER PUBLICATIONS

Gould et al., "A Numerical Evaluation of Sparse Direct Solvers for the Solution of Large Sparse Symmetric Linear Systems of Equations", ACM Transactions on Mathematical Software, vol. 33, No. 2, Article 10, Jun. 2007.

Johnson et al., "High-speed peak matching algorithm for retention time alignment of gas chromatographic data for chemometric analysis", Journal of Chromatography, 2003, 996, pp. 141-155.

(Continued)

*Primary Examiner* — Henry Tsai
*Assistant Examiner* — Aurangzeb Hassan
(74) *Attorney, Agent, or Firm* — Scully, Scott, Murphy & Presser, P.C.; Vazken Alexanian

(57) ABSTRACT

The problem of aligning multiple liquid chromatography mass spectrometry (LC-MS) runs to a common reference time frame is solved to facilitate comparison among LC-MS runs. The alignment of multiple LCMS can be achieved by solving a sparse system of linear equations to optimally stretch or compress local retention times for maximal similarity among the multiple runs. The multiple LCMS runs can be aligned simultaneously, thereby providing the advantage of efficient use of data by employing a sparse solver. A method of quality control in retention time alignment is also provided.

20 Claims, 5 Drawing Sheets

(56) References Cited

OTHER PUBLICATIONS

Kassidas et al., "Synchronization of Batch Trajectories Using Dynamic Time Warping", Process Systems Engineering, Apr. 1998, vol. 44, No. 4, pp. 864-875.
Katajamaa et al., "Processing methods for differential analysis of LC/MS profile data".
Kirchner et al., "amsrpm: Robust Point Matching for Retention Time Alignment of LC/MS Data with R", Journal of Statistical Software, Jan. 2007, vol. 18, Issue 4.
Li et al., "A Software Suite for the Generation and Comparison of Peptide Arrays from Sets of Data Collected by Liquid Chromatography-Mass Spectrometry", Molecular and Cellular Proteomics 4.9, 2005, pp. 1328-1340.
Listgarten et al., "Multiple Alignment of Continuous Time Series".
Listgarten et al., "Statistical and Computational Methods for Comparative Proteomic Profiling Using Liquid Chromatography-Tandem Mass Spectrometry", Molecular and Cellular Proteomics 4.4, 2005, pp. 419-434.
Nielsen et al., "Aligning of single and multiple wavelength chromatographic profiles for chemometric data nalysis using correlation optimised warping"m Journal of Chromatography A, 1998, 804, pp. 17-35.
Nordström et al., "Nonlinear Data Alignment for UPLC-MS and HPLC- MS Based Metabolomics: Quantitative Analysis of Endogenous and Exogenous Metabolites in Human Serum", Anal. Chem., 2006, 78, pp. 3289-3295.
Paige et al., "LSQR: An Algorithm for Sparse Linear Equations and Sparse Least Squares", ACM Transactions on Mathematical Software, Mar. 1982, vol. 8, No. 1, pp. 43-71.
Bellew et al., "A suite of algorithms for the comprehensive analysis of complex protein mixtures using high-resolution LC-MS", Bioinformatics, 2006, vol. 22, No. 15, pp. 1902-1909.
Bylund et al., "Chromatographic alignment by warping and dynamic programming as a pre-processing tool for PARAFAC modelling of liquid chromatography—mass spectrometry data", Journal of Chromatography, 2002, 961, pp. 237-244.
Eilers, "Parametric Time Warping", Anal. Chem., (Jan. 15, 2004), 76, pp. 404-411.
Fischer et al., "Semi-supervised LC/MS alignment for differential proteomics", Bioinformatics, 2006, vol. 22, No. 14, pp. e132-e140.
Prakash et al., "Signal Maps for Mass Spectrometry-based Comparative Proteomics", Molecular & Cellular Proteomics 5.3, 2006, pp. 423-432.
Pravdova et al., "A comparison of two algorithms for warping of analytical signals", Analytica Chimica Acta 456, 2002, pp. 77-92.
Prince et al., "Chromatographic Alignment of ESI-LC-MS Proteomics Data Sets by Ordered Bijective Interpolated Warping", Anal. Chem., Sep. 1, 2006, 78, pp. 6140-6152.
Radulovic et al., "Informatics Platform for Global Proteomic Profiling and Biomarker Discovery Using Liquid Chromatography—Tandem Mass Spectrometry", Molecular & Cellular Proteomics 3.10, 2004, pp. 984-997.
Suits et al., "Two-Dimensional Method for Time Aligning Liquid Chromatography—Mass Spectrometry Data", Anal. Chem., May 1, 2008, vol. 80, No. 9, pp. 3095-3104.
Wang et al., "Quantification of Proteins and Metabolites by Mass Spectrometry without Isotopic Labeling or Spiked Standards", Anal. Chem., Sep. 15, 2003, vol. 75, No. 18.
Wang et al., "A statistical method for chromatographic alignment of LC-MS data", Biostatistics, 2007, 8,2, pp. 357-367.
Wang et al., "Time-Warping Algorithm Applied to Chromatographic Peak Matching Gas Chromatography/Fourier Transform Infrared/Mass Spectrometry", Anal. Chem., 1987, 59, pp. 649-654.

* cited by examiner

US 8,635,258 B2

ALIGNMENT OF MULTIPLE LIQUID CHROMATOGRAPHY-MASS SPECTROMETRY RUNS

CROSS REFERENCE TO RELATED APPLICATION

This application is a continuation of U.S. patent application Ser. No. 12/546,966, filed Aug. 25, 2009 the entire content and disclosure of which is incorporated herein by reference.

BACKGROUND

This invention relates to an apparatus and a method of aligning multiple liquid chromatography-mass spectrometry (LC-MS) runs to a common reference time frame to facilitate comparison among runs. The present invention can employ a sparse solver to align multiple runs simultaneously, make efficient use of the data, and/or provide a means of quality control.

The retention time alignment problem is frequently encountered in LC-MS. As the main workhorse technology for large-scale protein profiling of biomedical samples, LC-MS has clinical applications such as the discovery of biomarker, e.g., markers that can predict disease states, sub-categories, or clinical outcome. Due to the huge number of proteins and their fragments present in biological samples, an LC-MS run routinely collects a large number of peaks (e.g., greater than $10^4$) within a couple of hours. Each peak has a mass, a retention time, and intensity. While the mass shift across different runs is typically small, the amount of shift in the retention time, i.e., the retention time shift, may be large and/or nonlinear. The retention times from each LC-MS run require sophisticated alignment to a common reference time frame to enable matching of peaks from different LC-MS runs.

Multiple methods have been developed to solve the retention time alignment problem. For example, F. Suits, et al., "Two-dimensional method for time aligning liquid chromatography-mass spectrometry data," Anal Chem, 80 (9), pp. 3095-104, (2008) discloses an example of a method, referred to as "Warp2D," for solving the retention time alignment. However, most methods, including Warp2D, provide only a pairwise alignment, i.e., alignment of a single LC-MS run to another LC-MS run.

To align multiple runs, most prior art methods align all runs to a common reference run, which is often arbitrarily chosen. An alternative approach is to align runs in a hierarchical fashion. In this approach, two most similar runs are merged in each step. The drawback of the hierarchical approach, like most tree-based approaches, is the accumulation and amplification of errors made in the early steps.

SUMMARY

In an embodiment of the present invention, the problem of aligning multiple liquid chromatography mass spectrometry (LC-MS) runs to a common reference time frame is solved to facilitate comparison among LC-MS runs. The alignment of multiple LC-MS is achieved by solving a sparse system of linear equations to optimally stretch or compress local retention times for maximal similarity among the multiple runs. The multiple LC-MS runs can be aligned simultaneously, thereby providing the advantage of efficient use of data by employing a sparse solver. A method of quality control in retention time alignment is also provided.

The method used in an embodiment of the present invention is a multiple alignment method that can achieve near optimal alignment using the comprehensive set of runs equally, thereby avoiding the arbitrary selection of a single reference run needed by pairwise approaches, and the accumulated errors of tree based methods. The method can analyze the full information collected in LC-MS runs, which includes a mass, an intensity, and a retention time for each peak.

An embodiment of the present invention provides a computer program using a sparse solver for time aligning multiple LC-MS runs of complex biological samples, including clinical samples of complex protein mixture. Another embodiment of the present invention provides a computer program using a sparse solver for quality control of retention time aligning multiple LC-MS runs of above-mentioned samples. Yet another embodiment of the present invention provides a computer program using a sparse solver for aligning multiple retention time series which are similar to each other, including voices, or financial time series.

According to an aspect of the present invention, a system for aligning peaks in liquid chromatography-mass spectroscopy (LC-MS) datasets from multiple runs to a common reference time frame is provided. The system includes a memory and a processor device in communication with the memory. The system is configured to perform a method including generating, for each LC-MS run in at least three LC-MS runs, a linear combination of a left-side adjacent node and a right-side adjacent node in a common reference time frame of the at least three LC-MS runs by employing the processor device and the memory to calculate the linear combination, wherein each of the left-side and right-side adjacent nodes is multiplied by a fixed coefficient, and the linear combination represents an approximation to a common retention time for a common peak across the least three LC-MS runs; generating, by employing the processor device and said memory, a linear system of equations that include equations that represent multiple pairwise alignments of the common peak across the at least three LC-MS runs, wherein the linear system of equations is stored in the memory; and solving, by employing the processor device and the memory, the linear system of equations for the left-side adjacent nodes and the right-side adjacent nodes to generate a solution that minimizes a fitting error, wherein the fixed coefficients remain constant and, the approximation to the common retention time for the common peak is determined by the solution as calculated by the processor device.

According to another aspect of the present invention, a method for aligning peaks in liquid chromatography-mass spectroscopy (LC-MS) datasets from multiple runs to a common reference time frame is provided. The method includes generating, for each LC-MS run in at least three LC-MS runs, a linear combination of a left-side adjacent node and a right-side adjacent node in a common reference time frame of the at least three LC-MS runs by employing the processor device and the memory to calculate the linear combination, wherein each of the left-side and right-side adjacent nodes is multiplied by a fixed coefficient, and the linear combination represents an approximation to a common retention time for a common peak across the least three LC-MS runs; generating, by employing the processor device and the memory, a linear system of equations that includes equations that represent multiple pairwise alignments of the common peak across the at least three LC-MS runs, wherein the linear system of equations is stored in the memory; and solving, by employing the processor device and the memory, the linear system of equations for the left-side adjacent nodes and the right-side adjacent nodes to generate a solution that minimizes a fitting error, wherein the fixed coefficients remain constant and, the approximation to the common retention time for the common peak is determined by the solution as calculated by the processor device.

According to yet another aspect of the present invention, a machine-readable data storage device embodying a program of machine-executable instructions to align peaks in liquid chromatography-mass spectroscopy (LC-MS) datasets from multiple runs to a common reference time frame is provided. The program includes the method that the system is configured to perform as described above.

DETAILED DESCRIPTION

Figure 1:
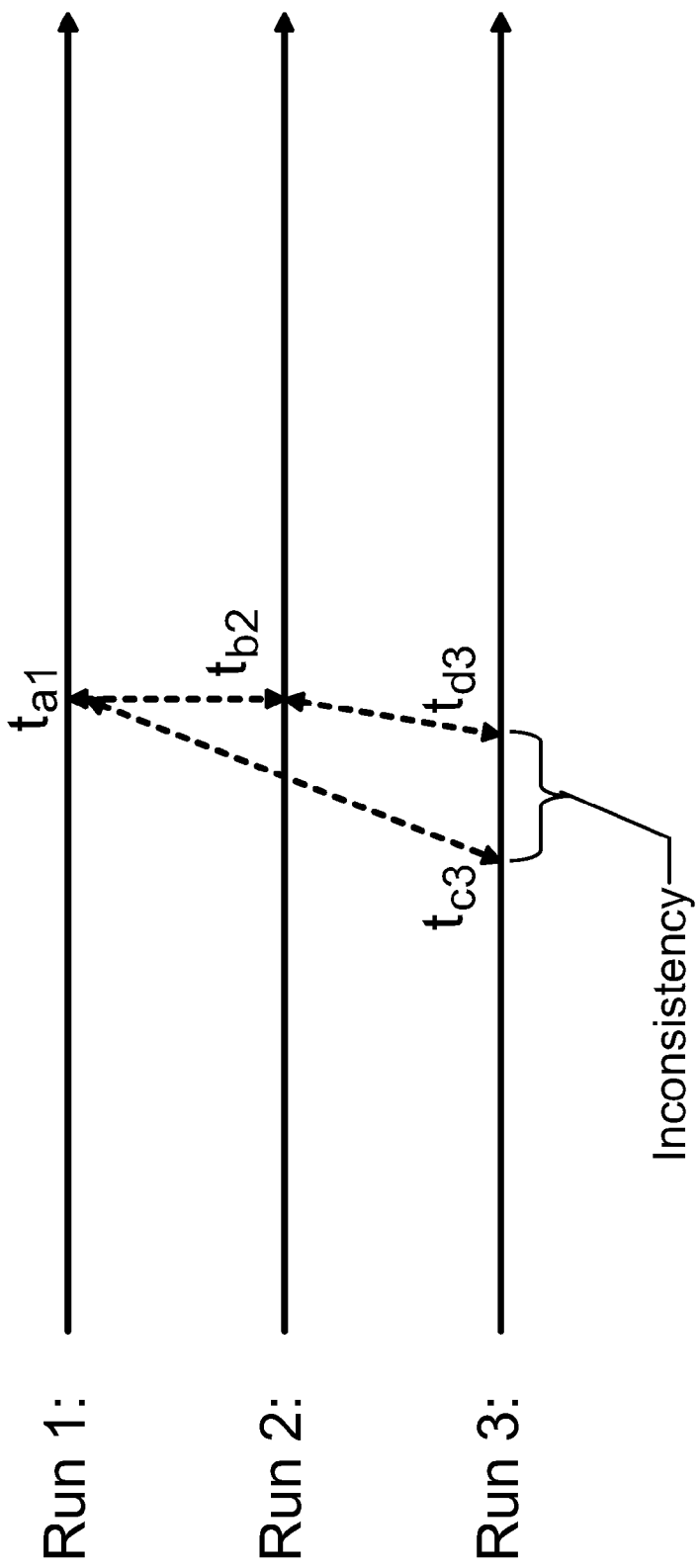
FIG. 1 is a schematic diagram illustrating a mechanism for inconsistency in matching peaks from at least three LC-MS runs through pairwise alignments. All retention times are in a common reference frame.

As stated above, the present invention relates to an apparatus and a method of aligning multiple liquid chromatography-mass spectrometry (LC-MS) runs to a common reference time frame, which are now described in detail with accompanying figures. The drawings are not necessarily drawn to scale.

As used herein, "liquid chromatography-mass spectroscopy" (LC-MS) is any technique that employs liquid chromatography and any type of mass spectroscopy.

As used herein, a "liquid chromatography-mass spectroscopy apparatus," or an "LC-MS apparatus" is any apparatus that generates data on LC-MS of a sample.

As used herein, an "LC-MS run" is an experiment on an LC-MS apparatus that generates an "LC-MS dataset," i.e., a dataset representing the LC-MS data from the experiment.

As used herein, a "liquid chromatography-mass spectroscopy database," or an "LC-MS database" is any database that stores at least one dataset from any LC-MS runs.

As used herein, a "retention time" is the time that a capillary column retains a particular compound that is detected as a peak in an LC-MS run. The retention time is the time between the starting time at which diffusion of a sample along a capillary column and the time at which an ionized molecule or an ion is detected by a mass spectrometer in an LC-MS apparatus.

As used herein, a "retention time frame" is a time frame that includes at least one retention time as a data point. A retention time frame can include a plurality of retention times as data points.

As used herein, a "peak" is a data point from an LC-MS run and represents presence of at least one compound in the material of the sample of the LC-MS run at a mass-to-charge ratio and at a retention time. Each peak in an LC-MS dataset has a unique combination of values for its mass-to-charge ratio and its retention time.

As used herein, a "total run time" of an LC-MS run is the length of time during which the LC-MS run is performed. All retention times are equal to or less than the total run time of the LC-MS run.

As used herein, a "section" of a retention time frame is a contiguous subset derived from dividing a contiguous portion of a retention time frame.

As used herein, a "node" is a point in time that corresponds to a partitioning point when a contiguous portion of a retention time frame is partitioned into sections.

As used herein, an "adjacent node" of a retention time is one of the two nodes in a retention time frame that does not have any other intervening node between the node and the retention time.

As used herein, a "linear combination" is a sum of scaled elements, i.e., a sum of products, in which each product is a product of a scalar and an element.

As used herein, a "common reference time frame" is a time frame that aligns retention time frames of multiple MC-LS runs so that a peak in the common reference time frame matches corresponding peaks in the time frames of multiple MC-LS runs.

As used herein, a "common retention time" is a point in a common reference time frame that represents a common peak among multiple MS-LS runs.

As used herein, a "pairwise" operation is an operation on a pair of elements that can be repeated for all possible pairs if more than three elements are present. Thus, a pairwise alignment of peaks is an alignment of a pair of peaks that can be repeated for every possible pair of peaks.

As used herein, a "memory" refers to a device, an apparatus, or a manufactured physical structure that is configured to store information and allow retrieval of the information.

As used herein, a "processor device" refers to a device, an apparatus, or a manufactured physical structure that includes an electronic circuit for processing data.

The present method of retention time alignment is named "Ensemble Alignment." Ensemble Alignment minimizes the inconsistency among multiple pairwise alignments by solving a system of sparse linear equations.

Referring to FIG. 1, corresponding peaks from three LC-MS runs are shown. Three pairwise alignments have been performed on the three peaks. A first retention time $t_{a1}$ in run 1 is aligned to a second retention time $t_{b2}$ in run 2 in a first pairwise alignment. The first retention time $t_{a1}$ in run 1 is also aligned to a third retention time $t_{c3}$ in run 3 in a second pairwise alignment. The second retention time $t_{b2}$ in run 2 is aligned to a fourth retention time $t_{d3}$ in run 3 in a third pairwise alignment between the run 2 and run 3. The first, second, and third retention times $t_{a1}$, $t_{b2}$, and $t_{c3}$ are in a hypothetical common reference retention time frame that is determined after alignment. The hypothetical common reference retention time frame is herein referred to as a common reference time frame.

The results of the three pairwise alignments can be expressed as a system of linear equations as follows:

$$t_{a1} = t_{b2}$$

$$t_{a1} = t_{c3}$$

$$t_{b2} = t_{d3}$$

Unless $t_{c3}$ and $t_{d3}$ are equal, this system of equations does not have a solution. Except in rare cases, there is always inconsistency among results of multiple pairwise alignments, simply because each pairwise alignment is only using the information from two runs at a time.

Ensemble Alignment can solve for a least square solution of the linear system using a sparse solver to minimize the inconsistency among the multiple pairwise alignments. The advantage of the least square approach is its effective use of information by taking all runs into account simultaneously, instead of two at a retention time. Ensemble Alignment is an effective method for summarize results from multiple pairwise alignment by minimizing the inconsistency among them.

Ensemble Alignment makes use of a piecewise linear approach. Since there can be an infinite number of retention time points in theory, it is computationally inefficient and sometimes impractical to treat each retention time point as an unknown. This piecewise approach divides a total run time of each run among at least three LC-MS runs into N sections with N+1 nodes. The N sections are separated by the N+1 nodes, and the N sections collectively constitute the total run time. N is an integer equal to or greater than 2, and is adjustable depending on the need for accuracy and computational capability of a system employed to perform the computation. Preferably, N is an integer equal to or greater than 10. For example, N can be an integer on the order of 50.

The N sections can be non-uniform, i.e., have different durations in time. Alternately, the N sections can be uniform, i.e., can have a same duration in time. In this case, the N sections can have a same duration in time given by $T_j/N$. Here, $T_j$ is a total run time for a j-th LC-MS run that include the N sections. The index j can run through all of the at least three LC-MS runs.

By expressing every retention time point in each run as a linear combination of the two neighboring nodes through linear interpolation, the number of unknowns for each run is reduced to N+1. This can be a significant reduction in the number of variables because the number of variables can be in the range of hundreds or thousands for data from one run if the retention time of each peak is treated as an independent variable.

Figure 2:
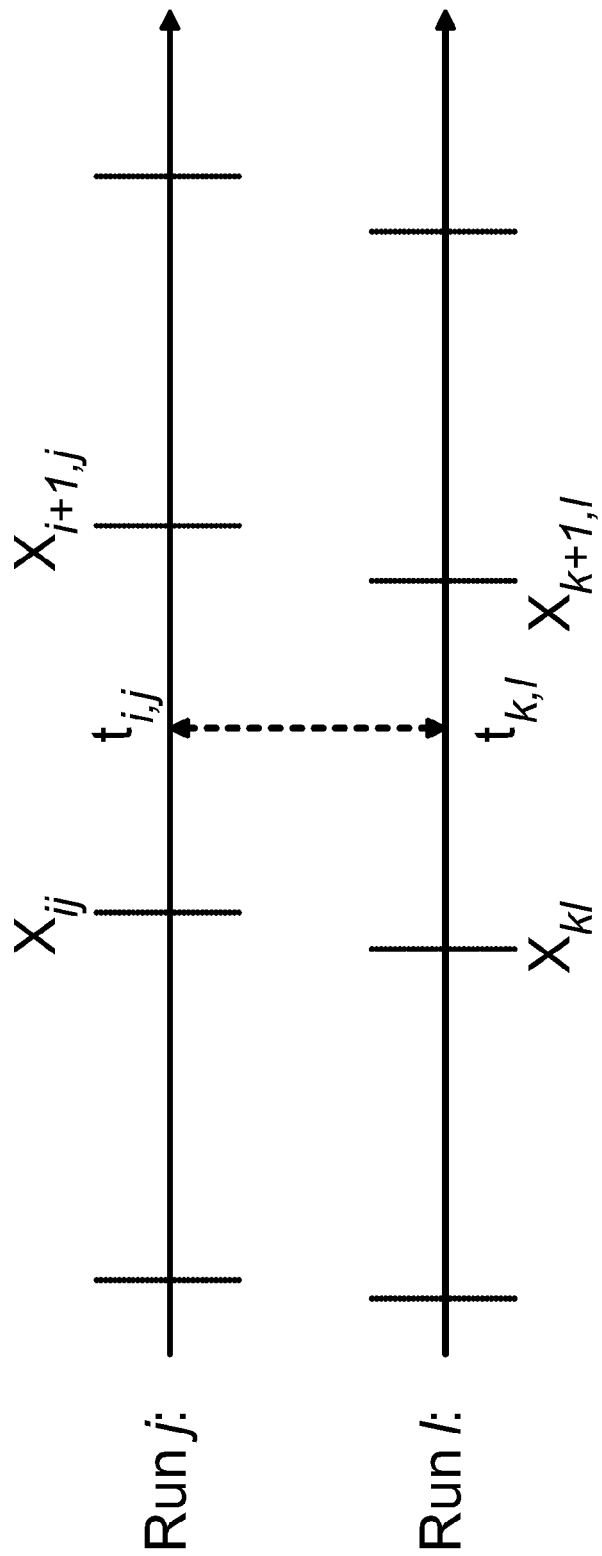
FIG. 2 is a schematic diagram illustrating how a retention time of a peak can be expressed in terms of the retention times of adjacent nodes in a piecewise linear fashion.

A large linear system can be formed by treating every peak and the retention time it is aligned to in a pairwise alignment as an equation. Referring to FIG. 2, for any peak with retention time $t_{ij}$ in run j which is aligned to retention time $t_{kl}$ in run l in a pairwise alignment, an equation can be written as follows:

$$t_{ij}=t_{kl}, \quad \text{eq. (1)}$$

where $t_{ij}$ and $t_{kl}$ are in a common reference time frame. Assuming retention time is linear between the two adjacent nodes, then $t_{ij}$ and $t_{kl}$ can be expressed as linear combinations of retention times at these nodes, for which the linear coefficients are invariant to changes of retention time frame and can be calculated in the original retention time frame.

Figure 3:
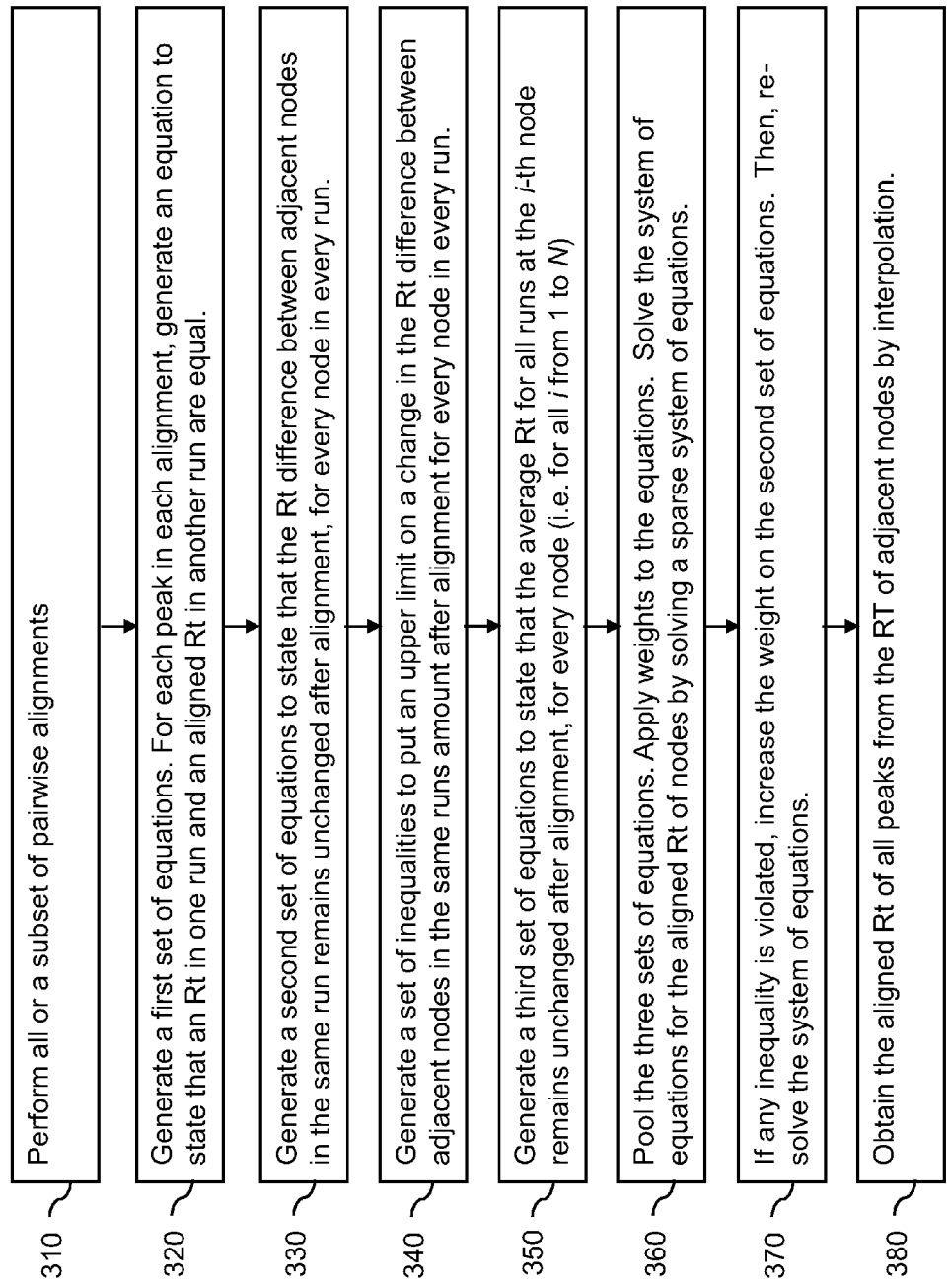
FIG. 3 is a flow chart illustrating the processing steps employed to generate data for aligning peaks from multiple LC-MS runs to a common reference time frame.

Referring to FIG. 3, a flow chart describes the processing steps employed to generate data for aligning peaks from multiple LC-MS runs to a common reference time frame employing illustrations for runs and equations. A system including at least one computing device can be employed to perform the steps of the flow chart in FIG. 3. The computing device can include a memory and a processor device in communication with the memory. The system is configured to align peaks in liquid chromatography-mass spectroscopy (LC-MS) datasets from multiple runs to a common reference time frame. The computing device can be configured to perform program instructions of the steps of the present invention. Each dataset includes peaks from an LC-MS run as a data point, which can include a mass, a retention time, and intensity.

Referring to step 310, pairwise alignments are performed on a set of peaks from at least three LC-MS runs. The peaks matched by the pairwise alignments can be all of the peaks in the at least three LC-MS runs, or can be a subset of the peaks that includes less than all peaks in the at least three LC-MS runs. For each LC-MS run in the at least three LC-MS runs, a linear combination of a "left-side adjacent node" and a "right-side adjacent node" in a common reference time frame of at least three LC-MS run can be generated. The left-side adjacent node is a node having a maximum value for time among all the nodes having a lesser or equal time than a peak in an original retention time frame of an LC-MS run within the at least three LC-MS runs. The right-side adjacent node is a node having a minimum value for time among all the nodes having a greater time than the peak in an original retention time frame of the LC-MS run. The original retention time frame is the time frame of the LC-MS run.

Each of the left-side and right-side adjacent nodes is multiplied by a fixed coefficient, and the linear combination represents an approximation to a common retention time for a common peak across the least three LC-MS runs. Further, for each LC-MS run in the at least three LC-MS runs, a plurality of linear combinations of a left-side adjacent node and a right-side adjacent node in a retention time frame of an LC-MS run can be generated. Each of the left-side adjacent node and the right-side adjacent node is multiplied by additional fixed coefficients. Each of the plurality of linear combinations represents a retention time for one of a plurality of common peaks across the least three LC-MS runs.

For example, the retention times of two neighboring nodes of $t_{ij}$ in run j can be denoted as $x_{ij}$ and $x_{i+1,j}$ in the common reference time frame. The ratio of the distance between $x_{ij}$ and $t_{ij}$ to the distance between $x_{ij}$ and $x_{i+1,j}$ in the original retention time frame for run j can be denoted as $f_{ij}$. Then $t_{ij}$ can be expressed as follows:

$$t_{ij}=(1-f_{ij})x_{ij}+f_{ij}x_{i+1,j}.$$

$t_{ij}$ represents a retention time for the common peak in a retention time frame of a j-th LC-MS run, $x_{ij}$ is an i-th node in the retention time frame of the j-the LC-MS run and is a left-side adjacent node of $t_{ij}$, $x_{i+1,j}$ is an (i+1)-th node in the retention time frame of the j-th LC-MS run and a right-side adjacent node of $t_{ij}$, $(1-f_{ij})$ is a first coefficient in the j-th LC-MS run, $f_{ij}$ is a second coefficient in the j-th LC-MS run, the $f_{ij}$ is a ratio of a distance between $x_{ij}$ and $t_{ij}$ to a distance between $x_{ij}$ and $x_{i+1,j}$ in the retention time frame of the j-th LC-MS run, and j is an index of one of at least three LC-MS runs. The first coefficient is multiplied to the left-side adjacent node, and the second coefficient is multiplied to the right-side adjacent node in each of the linear combinations. All coefficients are constants, and are not variables.

Likewise, the retention times of two neighboring nodes of $t_{kl}$ in run l can be denoted as $x_{kl}$ and $x_{k+1,l}$ in the common reference time frame. The ratio of the distance between $x_{kl}$ and $t_{kl}$ to the distance between $x_{kl}$ and $x_{k+1,l}$ in the original retention time frame for run l can be denoted as $f_{kl}$. Then $t_{kl}$ can be expressed as follows:

$$t_{kl}=(1-f_{kl})x_{kl}+f_{kl}x_{k+1,l}.$$

Referring to step 320, a first set of equations is generated. This can be effected by generating an equation to state, for each aligned pair of peaks, that a retention time (Rt) in one run and an aligned retention time (Rt) in another run are equal. Eq. (1) can be rewritten as:

$$(1-f_{ij})x_{ij}+f_{ij}x_{i+1,j}=(1-f_{kl})x_{kl}+f_{kl}x_{k+1,l}, \quad \text{eq. (2)}$$

in which $x_{ij}$ is an i-th node in a retention time frame of a j-th LC-MS run, $x_{i+1,j}$ is an (i+1)-th node in the retention time frame of the j-th LC-MS run, $(1-f_{ij})$ is a first coefficient in the j-th LC-MS run, $f_{ij}$ is a second coefficient in the j-th LC-MS run, $(1-f_{ij})x_{ij}+f_{ij}x_{i+1,j}$ represents a retention time for the common peak in a retention time frame of a j-th LC-MS run, $x_{kl}$ is a k-th node in a retention time frame of an l-th LC-MS run, $x_{k+1,l}$ is a (k+1)-th node in the retention time frame of the l-th LC-MS run, $(1-f_{kl})$ is a first coefficient in the l-th LC-MS run, $f_{k+1,l}$ is a second coefficient in the l-th LC-MS run, $(1-f_{kl})x_{kl}+f_{kl}x_{k+1,l}$ represents a retention time for the common peak in a retention time frame of an l-th LC-MS run, and j and l are different indices of runs within the at least three LC-MS runs.

For a given value of j and l, Eq. (2) contains four unknowns, i.e., retention times of the four nodes in the original retention time frame. $f_{ij}$ and $f_{kl}$ are known coefficients calculated from the original retention time frames, i.e., the retention time frames of the j-th run and the l-th run. One equation from eq. (2) represents a matching of one common peak in one pairwise alignment.

A linear system of equations that includes equations that represent multiple pairwise alignments of the common peak across the at least three LC-MS runs can be generated. This operation can be performed for every common peak that can be matched. Thus, the system of equations can include equations for every peak employed in all pairwise alignments involving the at least three LC-MS run. For each LC-MS run in the at least three LC-MS runs, a plurality of linear combinations of a left-side adjacent node and a right-side adjacent node in the common reference time frame can be generated. Each of the left-side adjacent node and the right-side adjacent node is multiplied by additional fixed coefficients. Each of the plurality of linear combinations represents an approximation to a common retention time for one of a plurality of common peaks across the least three LC-MS runs.

The total number of LC-MS runs can be denoted as M. Each matched peak can generate M×(M−1)/2 number of equations because the number of equations that a peak can generate is the number of possible pairwise matching of the common peaks among the at least three LC-MS runs. If the average number of peaks in M LC-MS runs is Q, then the total number of equations that can be generated from eq. (2) is approximately Q×M×(M−1)/2. However, the total number of unknowns in a set of linear equations given by eq. (2) is capped at (N+1)×M irrespective of the number of peaks in M LC-MS runs. The cap on the number of unknowns to be determined in the linear system of equations places a limit on the complexity of the system to be solved.

Thus, eq. (2) generates a first set of equations to the linear system of equations. All of the approximately Q×M×(M−1)/2 equations, or only a subset less than all of the equations, can be added to the linear system of equations.

Two important constraints can be added, either singly or in combination, to the linear system of equations prior to solving the system of linear equations. The first constraint is a slack parameter s to restrict the amount of adjustment allowed between two adjacent nodes. This parameter is common for all piecewise linear alignment methods.

Referring to step 330, a second set of equations can be generated to state that the retention time (Rt) difference between adjacent nodes in the same run remains unchanged after alignment, for every node in every run. For all N+1 nodes in run j which has a total retention time duration of $T_j$, the following linear equations are added to the system:

$$w(x_{i+1,j}-x_{ij})=wT_j/N \qquad \text{eq. (3)}$$

for every i from 0 to N and for every run. w is an adjustable weight factor common for all equations and can be initially set to 1. $x_{ij}$ is a left-side adjacent node in the retention time frame of the j-th LC-MS run, $x_{i+1,j}$ is a right-side adjacent node in the retention time frame of the j-th LC-MS run, and j is an index that runs through all of the at least three LC-MS runs. Eq. (3) is a second set of linear equations that are added to the linear system of equations.

Referring to step 340, a set of inequalities can be generated to put an upper limit on a change in the retention time (Rt) difference between adjacent nodes in the same runs after alignment for every node in every run. The inequalities can be in the form of:

$$|x_{i+1,j}-x_{ij}-(T_j/N)|\leq s, \qquad \text{eq. (4)}$$

in which s is a slack parameter that limits an amount of adjustment allowed between two adjacent nodes. After an initial least square solution for the system of equations is found, the initial least square solution can be checked to determine if the inequality in eq. (4) is violated for any combination of i and j.

If the inequality in eq. (4) is violated for any i between 0 and N or for any run with the run index j between 1 and M by a solution the system of linear equations, w can be increased to re-solve the linear system until all inequalities of eq. (4) are satisfied by a solution.

A second constraint can be added in order to set an absolute reference retention time frame. Without the setting of an absolute reference retention time frame, i.e., a common reference time frame, an infinite number of least square solutions would exist which are equally good because all retention times would be relative to each other. The absolute retention time frame can be either set to that of any of the runs, or set to an average of all retention time frames of the at least three LC-MS runs.

In one embodiment, the common reference time frame can be set as one of retention time frames of the at least three LC-MS runs.

In another embodiment, the common reference time frame can be set to the average of all retention time frames of the at least three LC-MS runs. Referring to step 350, a third set of equations can be generated to state that the average retention time (Rt) for all runs at the i-th node remains unchanged after alignment, for every node, i.e. for all values of i from 1 to N. For example, the following equations can be added to the system:

$$\lambda\sum_{j=1}^{M} x_{ij} = \lambda\sum_{j=1}^{M} i(T_j/N). \qquad \text{eq. (5)}$$

$\lambda$ is a constant weight that operates as a weighting parameter for the additional equations in the linear system of equations, M is a total number of the at least three LC-MS runs, $x_{ij}$ is a left-side adjacent node in a retention time frame of the j-th LC-MS run, $x_{i+1,j}$ is a right-side adjacent node in the retention time frame of the j-th LC-MS run, and j is an index that runs through all of the at least three LC-MS runs. $x_{ij}$ is also the retention time of the i-th node in the j-th LC-MS run in the common reference time frame, and $x_{i+1,j}$ is also the retention time of the (i+1)-th node in the j-th LC-MS run in the common reference time frame. $\lambda$ is set to a very large number, e.g., 1,000, to ensure that the absolute retention time frame is the average retention time of all runs. In essence, eq. (5) applies the constraint that the average retention time at the ith node in the common frame is the same as the average at the same node in the original retention time frames.

Referring to step 360, a linear system of equations is generated by combining the equations provided above. The linear system of equations includes equations given by eq. (2) and eq. (3), and optionally includes the equations given by eq. (5). The linear system of equations includes the two sets of equations given by eq. (2) and eq. (3), or the three sets of equations given by eq. (2), eq. (3), and eq. (5). The equations are weighted employing the parameters s, w, and $\lambda$. The system of equations can be solved for the aligned retention time (Rt) of nodes by solving a sparse system of equations.

Referring to step 370, the solution is checked if any of the inequalities in eq. (4) is violated. If any inequality in eq. (4) is violated, the weight on the second set of equations in eq. (3) is increased. Then, the linear system of equations is re-solved for a new solution.

Referring to step 380, the aligned retention time (Rt) is obtained for all common peaks from the retention times of adjacent nodes by interpolation. The fixed coefficients in the linear combinations that represent an approximation to a common retention time in combination with values for the nodes as determined by the solution provides the common retention time for each common peak in the common reference time frame.

Figure 4:
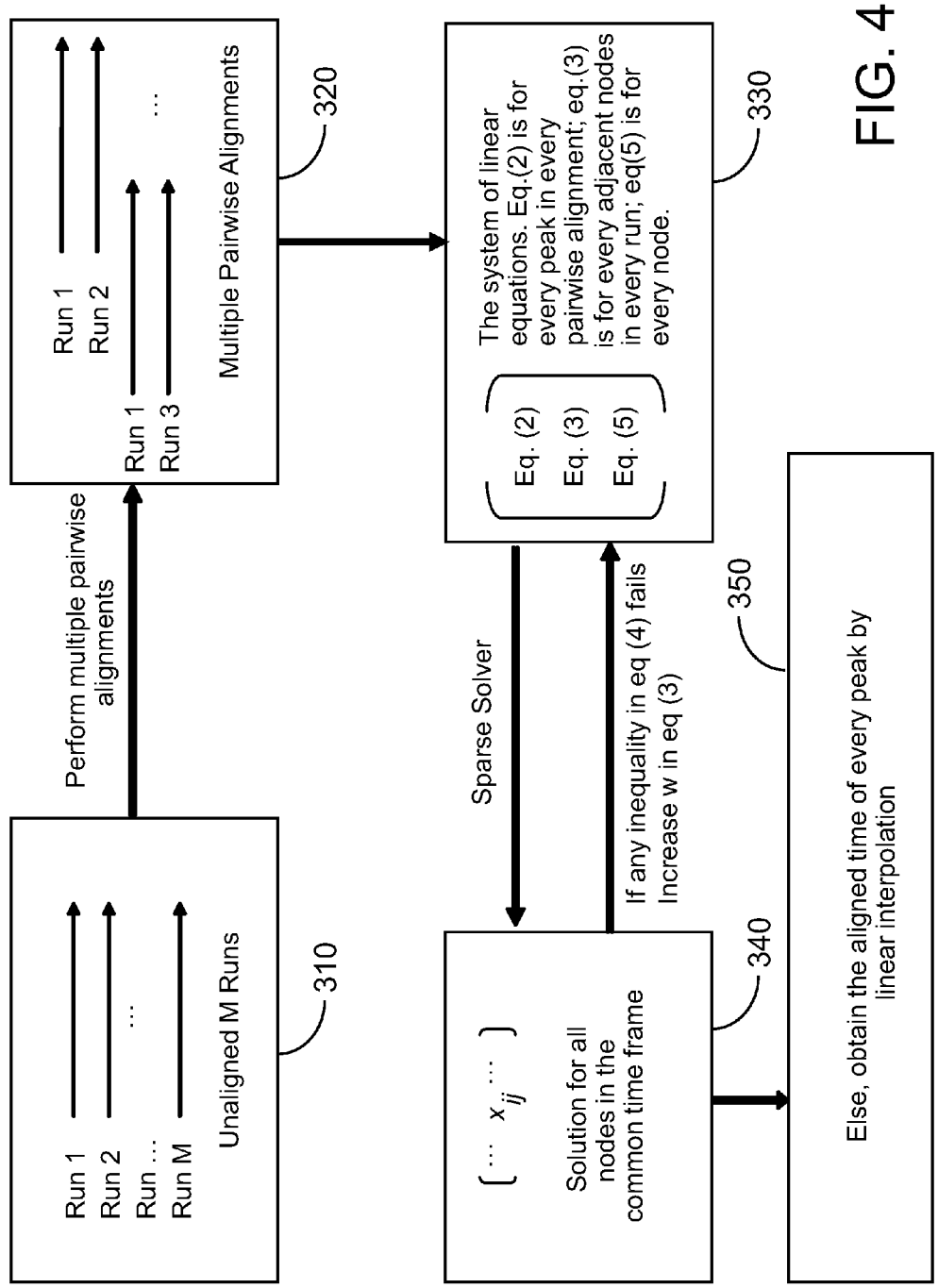
FIG. 4 is another flow chart illustrating the processing steps in the flow chart of FIG. 3 with a detailed description of an adjustment mechanism for a slack parameter s.

Referring to FIG. 4, another flow chart illustrates the processing steps in the flow chart of FIG. 3 with a detailed description of an adjustment mechanism for a slack parameter s.

Referring to step 410, datasets from at least three LC-MS runs are provided as an input to the system. The at least three LC-MS runs are unaligned as provided.

Referring to step 420, multiple pairwise alignments are performed as described above. This step generates a linear system of equations including all equations in eq. (2), which represent all pairwise alignment for all peaks.

Referring to step 430, additional equations are added to the linear system of equations. The added equations can include all equations in eq. (3), which represent the slack constraint, and/or all equations in eq. (5), which set the absolute retention time frame. Eq. (5) is subject to a subsequent verification of the inequality constraints in (3), which can be checked after a solution is found. The adjustable parameters include the slack parameter s that restricts the amount of adjustment allowed between two adjacent nodes in eq. (4), the adjustable weight factor w that is employed to enforce the inequality constraints in eq. (3), and/or the constant weight $\lambda$ that enforces that the absolute retention time frame is the average of all runs in eq. (5).

Referring to step 440, the linear system of equations is solved for all nodes of the at least three LC-MS runs including the left-side adjacent nodes and the right-side adjacent nodes of each $x_{ij}$ for every combination of i and j that is present in the linear system of equations. For example, the linear system of equations can be solved by employing at least one of a sparse solver and a stochastic method. A goodness of fit of the solution can be determined employing a statistical test such as chi-squared test.

Solving the linear system of equations determines an approximation to the common retention time for the common peak. The generated solution minimizes a fitting error for the determination of a common retention time for the common peak in the common reference time frame. All of the fixed coefficients representing each $x_{ij}$ for every combination of i and j that is present in the linear system of equations remain constant during the generation of the solution.

The solution can minimize a sum of squared differences in the linear system of equations. In this case, each of the squared differences is a square of a difference between the common retention time and a retention time that one of the linear combinations represents.

The inequalities in eq. (4) can be checked once a solution is provided. If any of the inequalities in eq. (4) is violated, the process flow proceeds to step 430 to increase the slack parameter. After the adjustment of the slack parameter s, the process flow proceeds to step 440 to re-solve the linear system of equations.

If the all of the inequalities in eq. (4) are satisfied, the process flow proceeds to step 450, at which the solution to the linear system of equations is finalized, and all peaks in the at least three LC-MS runs are aligned in the common reference time frame.

Computationally, the linear equation system can be solved by a sparse solver because only several nodes are involved in any equation derived from eq. (2). The sparse solver enables a large number of peaks and pairwise alignment to be considered simultaneously. A trial run demonstrated that Ensemble Alignment improves alignment accuracy by about 20% compared to Warp2D.

Figure 5:
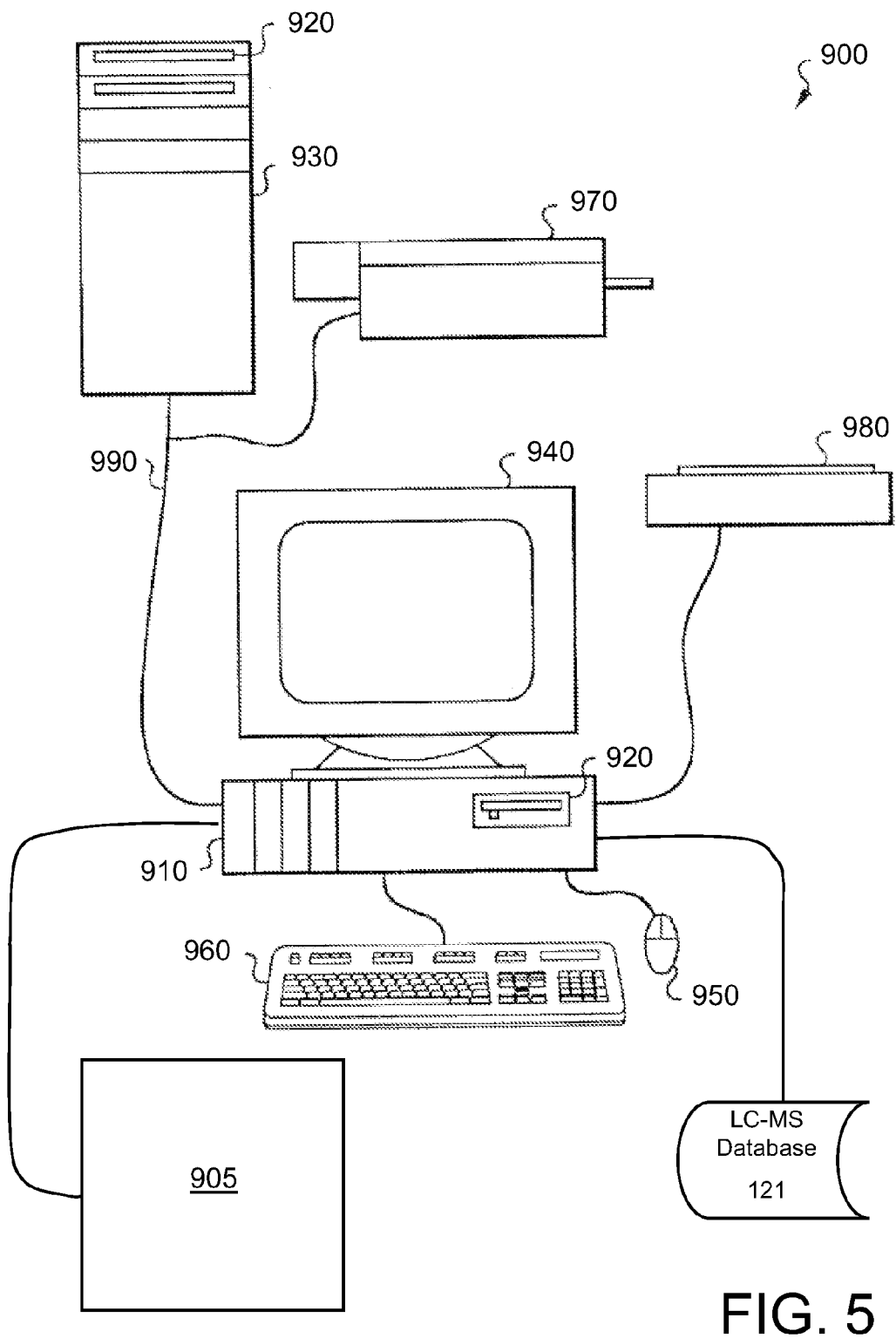
FIG. 5 illustrates an exemplary system according to an embodiment of the present invention.

Referring to FIG. 5, an exemplary system 900 according to the present invention is shown. The exemplary system 900 can be employed for matching peaks in liquid chromatography-mass spectroscopy (LC-MS) datasets from multiple runs. The exemplary system includes a computing device that is configured to perform program instructions. The computing device can include a memory and a processor device in communication with the memory. The program instructions can configure the computing device to perform the steps of embodiments of the present invention described above. The exemplary system 900 can be a computer-based system in which the methods of the embodiments of the invention can be carried out by an automated program of machine-executable instructions to match peaks in liquid chromatography-mass spectroscopy (LC-MS) datasets from multiple runs.

A data storage device that is programmable and readable by a machine and tangibly embodying or storing a program of instructions that are executable by the machine to perform the methods described herein are also provided. For example, the automated program can be embodied, i.e., stored, in a machine-readable data storage devices such as a hard disk, a CD ROM, a DVD ROM, a portable storage device having an interface such as a USB interface, a magnetic disk, or any other storage medium suitable for storing digital data.

The computer-based system includes a processing unit 910, which is a computing device and houses a processor device, a memory and other systems components (not shown expressly in the drawing) that implement a general purpose or special purpose processing system, or computer that can execute a computer program product. The computer program product can comprise media, for example a compact storage medium such as a compact disc, which can be read by the processing unit 910 through a disc drive 920, or by any means known to the skilled artisan for providing the computer program product to the general purpose processing system for execution thereby. The exemplary system 900 can include an LC-MS apparatus 905 and/or an LC-MS database. Alternately, the LC-MS apparatus 905 and/or an LC-MS database 121 can be external to the exemplary system 900 and electronically connected through a wired network or a wireless network.

The computer program product can comprise all the respective features enabling the implementation of the inventive method described herein, and which is able to carry out the method when loaded in a computer system. Computer program, software program, program, or software, in the present context means any expression, in any language, code or notation, of a set of instructions intended to cause a system having an information processing capability to perform a particular function either directly or after either or both of the following: (a) conversion to another language, code or notation; and/or (b) reproduction in a different material form.

The computer program product can be stored on hard disk drives within the processing unit 910, as mentioned, or can be located on a remote system such as a server 930, coupled to the processing unit 910, via a network interface such as an Ethernet interface. A monitor 940, a mouse 950 and a keyboard 960 are coupled to the processing unit 910, to provide user interaction. A scanner 980 and a printer 970 can be provided for document input and output. The printer 970 is shown coupled to the processing unit 910 via a network connection, but can be coupled directly to the processing unit 910. The scanner 980 is shown coupled to the processing unit 910 directly, but it should be understood that peripherals might be network coupled, or direct coupled without affecting the ability of the processing unit 910 to perform the method of the invention.

While the present invention has been particularly shown and described with respect to preferred embodiments thereof, it will be understood by those skilled in the art that the foregoing and other changes in forms and details can be made without departing from the spirit and scope of the present invention. For example, variations that combine various steps of the first, second, and third exemplary programs in a single program can be employed. It is therefore intended that the present invention not be limited to the exact forms and details described and illustrated, but fall within the scope of the appended claims.

What is claimed is:

1. A method for aligning peaks in liquid chromatography-mass spectroscopy (LC-MS) datasets from multiple runs to a common reference time frame, said method comprising:
generating, for each selected LC-MS run in at least three LC-MS runs, a linear combination of a first retention time at a left-side adjacent node and a second retention time at a right-side adjacent node in a common reference time frame of said at least three LC-MS run by employing said processor device and said memory to calculate said linear combination, wherein said first retention time at said left-side adjacent node is multiplied by a first coefficient and said second retention time at said right-side adjacent node is multiplied by a second coefficient within said linear combination such that a sum of said first coefficient and said second coefficient is equal to 1, and said linear combination represents an approximation to a common retention time for a common peak across said least three LC-MS runs;
generating, by employing said processor device and said memory, a linear system of equations that includes equations that represent multiple pairwise alignments of said common peak across said at least three LC-MS runs, wherein said linear system of equations is stored in said memory; and
solving, by employing said processor device and said memory, said linear system of equations for said left-side adjacent nodes and said right-side adjacent nodes to generate a solution that minimizes a fitting error, wherein said fixed coefficients remain constant and, said approximation to said common retention time for said common peak is determined by said solution as calculated by said processor device.

2. The method of claim 1, further comprising dividing, by employing said processor device and said memory, a total run time of each run into N sections separated by N+1 nodes, wherein N is an integer equal to or greater than 2, wherein said N sections have a same duration in time, and is given by Tj/N, wherein Tj is a total run time for a j-th LC-MS run that include said N sections.

3. The method of claim 2, wherein said linear system of equations further includes additional equations given by $w(x_{i+1,j}-x_{ij})=wT_j/N$, wherein w is a weight factor, $x_{ij}$ is a left-side adjacent node in a retention time frame of said j-th LC-MS run, $x_{i+1,j}$ is a right-side adjacent node in said retention time frame of said j-th LC-MS run, and j is an index that runs through all of said at least three LC-MS runs.

4. The method of claim 2, wherein said linear system of equations further includes additional equations given by $$\lambda \sum_{j=1}^{M} x_{ij} = \lambda \sum_{j=1}^{M} i(T_j/N),$$

wherein $\lambda$ is a constant weight that operates as a weighting parameter for said additional equations in said linear system of equations, M is a total number of said at least three LC-MS runs, $x_{ij}$ is a left-side adjacent node in a retention time frame of said j-th LC-MS run, $x_{i+1,j}$ is a right-side adjacent node in said retention time frame of said j-th LC-MS run, and j is an index that runs through all of said at least three LC-MS runs.

5. The method of claim 1, wherein each of said equations that represent multiple pairwise alignments is given by $(1-f_{ij})x_{ij}+f_{ij}x_{i+1,j}=(1-f_{kl})x_{kl}+f_{kl}x_{k+1,l}$, wherein $x_{ij}$ is an i-th node in a retention time frame of a j-th LC-MS run, $x_{i+1,j}$ is an (i+1)-th node in said retention time frame of said j-th LC-MS run, $(1-f_{ij})$ is a first coefficient in said j-th LC-MS run, $f_{ij}$ is a second coefficient in said j-th LC-MS run, $(1-f_{ij})x_{ij}+f_{ij}x_{i+1,j}$ represents a retention time for said common peak in a retention time frame of a j-th LC-MS run, $x_{kl}$ is a k-th node in a retention time frame of an l-th LC-MS run, $x_{k+1,l}$ is a (k+1)-th node in said retention time frame of said l-th LC-MS run, $(1-f_{kl})$ is a first coefficient in said l-th LC-MS run, $f_{k+1,l}$ is a second coefficient in said l-th LC-MS run, $(1-f_{kl})x_{kl}+f_{kl}x_{k+1,l}$ represents a retention time for said common peak in a retention time frame of an l-th LC-MS run, and j and l are different indices of runs within said at least three LC-MS runs.

6. A machine-readable data storage device embodying a program of machine-executable instructions to align peaks in liquid chromatography-mass spectroscopy (LC-MS) datasets from multiple runs to a common reference time frame, wherein said program includes steps for:
generating, for each selected LC-MS run in at least three LC-MS runs, a linear combination of a first retention time at a left-side adjacent node and a second retention time at a right-side adjacent node in a common reference time frame of said at least three LC-MS run by employing said processor device and said memory to calculate said linear combination, wherein said first retention time at said left-side adjacent node is multiplied by a first coefficient and said second retention time at said right-side adjacent node is multiplied by a second coefficient within said linear combination such that a sum of said first coefficient and said second coefficient is equal to 1, and said linear combination represents an approximation to a common retention time for a common peak across said least three LC-MS runs;

generating, by employing said processor device and said memory, a linear system of equations that include equations that represent multiple pairwise alignments of said common peak across said at least three LC-MS runs, wherein said linear system of equations is stored in said memory; and solving, by employing said processor device and said memory, said linear system of equations for said left-side adjacent nodes and said right-side adjacent nodes to generate a solution that minimizes a fitting error, wherein said fixed coefficients remain constant and, said approximation to said common retention time for said common peak is determined by said solution as calculated by said processor device.

7. The machine-readable data storage device of claim 6, wherein said program further comprises dividing, by employing said processor device and said memory, a total run time of each run into N sections separated by N+1 nodes, wherein N is an integer equal to or greater than 2, wherein said N sections have a same duration in time, and is given by $T_j/N$, wherein $T_j$ is a total run time for a j-th LC-MS run that include said N sections.

8. The machine-readable data storage device of claim 7, wherein said linear system of equations further includes additional equations given by $w(x_{i+1,j}-x_{ij})=wT_j/N$, wherein w is a weight factor, $x_{ij}$ is a left-side adjacent node in a retention time frame of said j-th LC-MS run, $x_{i+1,j}$ is a right-side adjacent node in said retention time frame of said j-th LC-MS run, and j is an index that runs through all of said at least three LC-MS runs.

9. The machine-readable data storage device of claim 7, wherein said linear system of equations further includes additional equations given by $$\lambda \sum_{j=1}^{M} x_{ij} = \lambda \sum_{j=1}^{M} i(T_j/N),$$

wherein $\lambda$ is a constant weight that operates as a weighting parameter for said additional equations in said linear system of equations, M is a total number of said at least three LC-MS runs, $x_{ij}$ is a left-side adjacent node in a retention time frame of said j-th LC-MS run, $x_{i+1,j}$ is a right-side adjacent node in said retention time frame of said j-th LC-MS run, and j is an index that runs through all of said at least three LC-MS runs.

10. The machine-readable data storage device of claim 6, wherein each of said equations that represent multiple pairwise alignments is given by 0.

11. The method of claim 1, wherein, for each LC-MS run in said at least three LC-MS runs, said linear combinations is given by: $t_{ij}=(1-f_{ij})x_{ij}+f_{ij}x_{i+1,j}$, wherein $t_{ij}$ represents a retention time for said common peak in a retention time frame of a j-th LC-MS run, $x_{ii}$ is an i-th node in said retention time frame of said j-the LC-MS run and is a left-side adjacent node of $t_{ij}$, $x_{i+1,j}$ is an (i+1)-th node in said retention time frame of said j-th LC-MS run and a right-side adjacent node of $t_{ij}$, $(1-f_{ij})$ is a first coefficient in said j-th LC-MS run, $f_{ij}$ is a second coefficient in said j-th LC-MS run, said $f_{ij}$ is a ratio of a distance between $x_{ij}$ and $t_{ij}$ to a distance between $x_{ij}$ and $x_{i+1,j}$ in said retention time frame of said j-th LC-MS run, and j is an index that runs through all of said at least three LC-MS runs.

12. The method of claim 1, wherein said solution minimizes a sum of squared differences in said linear system of equations, and each of said squared differences is a square of a difference between said common retention time and a retention time that one of said linear combinations represents.

13. The method of claim 1, further comprising dividing, by employing said processor device and said memory, a total run time of each run into N sections separated by N+1 nodes, wherein N is an integer equal to or greater than 2, wherein said N sections have different durations in time.

14. The method of claim 3, wherein said method further includes determining, by employing said processor device and said memory, whether an inequality is violated for said solution, wherein said inequality is given by $|x_{i+1,j}-x_{ij}-(T_j/N)|\leq s$, wherein s is a slack parameter that limits an amount of adjustment allowed between two adjacent nodes.

15. The method of claim 14, wherein said method further includes the step of increasing, by employing said processor device and said memory, a value for said weight factor w if said inequality is violated for said solution.

16. The method of claim 3, wherein said method further includes setting said common reference time frame as one of retention time frames of said at least three LC-MS runs.

17. The method of claim 1, wherein said method further includes generating, for each LC-MS run in said at least three LC-MS runs, a plurality of linear combinations of a left-side adjacent node and a right-side adjacent node in said common reference time frame by employing said processor device and said memory to calculate said linear combination, wherein each of said left-side adjacent node and said right-side adjacent node is multiplied by additional fixed coefficients, and each of said plurality of linear combinations represents an approximation to a common retention time for one of a plurality of common peaks across said least three LC-MS runs.

18. The method of claim 1, wherein said left-side adjacent node is a node having a maximum value for time among all nodes having a lesser or equal time than a peak in a retention time frame of said selected LC-MS run that corresponds to said common peak, and said right-side adjacent node is a node having a minimum value for time among all nodes having a greater time than said peak in said retention time frame of said selected LC-MS run.

19. The machine-readable data storage device of claim 6, wherein, for each LC-MS run in said at least three LC-MS runs, said linear combinations is given by: $t_{ij}=(1-f_{ij})x_{ij}+f_{ij}x_{i+1,j}$, wherein $t_{ij}$ represents a retention time for said common peak in a retention time frame of a j-th LC-MS run, $x_{ij}$ is an i-th node in said retention time frame of said j-the LC-MS run and is a left-side adjacent node of $t_{ij}$, $x_{i+1,j}$ is an (i+1)-th node in said retention time frame of said j-th LC-MS run and a right-side adjacent node of $t_{ij}$, $(1-f_{ij})$ is a first coefficient in said j-th LC-MS run, $f_{ij}$ is a second coefficient in said j-th LC-MS run, said $f_{ij}$ is a ratio of a distance between $x_{ij}$ and $t_{ij}$ to a distance between $x_{ij}$ and $x_{i+1,j}$ in said retention time frame of said j-th LC-MS run, and j is an index that runs through all of said at least three LC-MS runs.

20. The machine-readable data storage device of claim 6, wherein said left-side adjacent node is a node having a maximum value for time among all nodes having a lesser or equal time than a peak in a retention time frame of said selected LC-MS run that corresponds to said common peak, and said right-side adjacent node is a node having a minimum value for time among all nodes having a greater time than said peak in said retention time frame of said selected LC-MS run.

* * * * *